United States Patent
Horihata et al.

(10) Patent No.: US 12,123,110 B2
(45) Date of Patent: Oct. 22, 2024

(54) FIBER FOR ARTIFICIAL HAIR, HEAD ACCESSORY PRODUCT, AND RESIN COMPOSITION FOR ARTIFICIAL HAIR

(71) Applicant: DENKA COMPANY LIMITED, Tokyo (JP)

(72) Inventors: Atsushi Horihata, Tokyo (JP); Takashi Muraoka, Tokyo (JP); Atsushi Takei, Tokyo (JP)

(73) Assignee: DENKA COMPANY LIMITED, Tokyo (JP)

( * ) Notice: Subject to any disclaimer, the term of this patent is extended or adjusted under 35 U.S.C. 154(b) by 539 days.

(21) Appl. No.: 17/423,749

(22) PCT Filed: Feb. 12, 2020

(86) PCT No.: PCT/JP2020/005371
§ 371 (c)(1),
(2) Date: Jul. 16, 2021

(87) PCT Pub. No.: WO2020/166614
PCT Pub. Date: Aug. 20, 2020

(65) Prior Publication Data
US 2022/0117341 A1    Apr. 21, 2022

(30) Foreign Application Priority Data

Feb. 14, 2019 (JP) ................ 2019-024819

(51) Int. Cl.
*D01F 6/60* (2006.01)
*A41G 3/00* (2006.01)
*C08K 3/34* (2006.01)
*D01F 1/10* (2006.01)
*D01F 8/12* (2006.01)
*D01F 8/16* (2006.01)

(52) U.S. Cl.
CPC .......... *D01F 6/60* (2013.01); *C08K 3/34* (2013.01); *D01F 1/10* (2013.01); *D01F 8/12* (2013.01); *D01F 8/16* (2013.01); *A41G 3/0083* (2013.01); *D10B 2331/02* (2013.01); *D10B 2503/08* (2013.01)

(58) Field of Classification Search
None
See application file for complete search history.

(56) References Cited

U.S. PATENT DOCUMENTS 4,781,647 A * 11/1988 Doane, Jr. .............. C09K 11/02
446/385

FOREIGN PATENT DOCUMENTS

| JP | S48-40689 A | | 6/1973 |
|---|---|---|---|
| JP | 2007-303014 A | | 11/2007 |
| JP | 2007-332507 A | | 12/2007 |
| JP | 2011-246843 A | | 12/2011 |
| JP | 2011246843 | * | 12/2011 |
| JP | 2012-12423 A | | 1/2012 |
| JP | 2012-012738 A | | 1/2012 |
| JP | 2012012738 | * | 1/2012 |
| WO | WO9946327 | * | 9/1999 |
| WO | 2006/121054 A1 | | 11/2006 |
| WO | 2010/134581 A1 | | 11/2010 |
| WO | WO2018187638 | * | 10/2018 |

OTHER PUBLICATIONS

Machine Translation of JP2012012738 (Year: 2012).*
Machine Translation of JP2011246843 (Year: 2011).*
Oct. 24, 2023 Office Action Issued in Japanese Patent Application No. 2020-572279.
Jul. 8, 2022 Office Action and Search Report issued in Chinese Patent Application No. 202080009759.X.
Mar. 10, 2020 International Search Report issued in International Patent Application No. PCT/JP2020/005371.
Dec. 5, 2023 Notice of Allowance issued in Japanese Application 2020-572279.

* cited by examiner

*Primary Examiner* — Shawn Mckinnon
(74) *Attorney, Agent, or Firm* — Oliff PLC

(57) ABSTRACT

A fiber for artificial hair is constituted of a resin composition containing an aliphatic polyamide and inorganic particles, and in a particle size distribution of the inorganic particles measured by a laser diffraction method, a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more and 3.0 or less.

17 Claims, No Drawings

FIBER FOR ARTIFICIAL HAIR, HEAD ACCESSORY PRODUCT, AND RESIN COMPOSITION FOR ARTIFICIAL HAIR

TECHNICAL FIELD

The present invention relates to a fiber for artificial hair, a head accessory product, and a resin composition for artificial hair.

BACKGROUND ART

As a material constituting a fiber for artificial hair, there is polyamide. Patent Document 1 discloses a fiber for artificial hair obtained by fiberizing a resin composition containing polyamide.

RELATED DOCUMENT

Patent Document

[Patent Document 1] Japanese Unexamined Patent Publication No. 2011-246843

SUMMARY OF THE INVENTION

Technical Problem

A fiber for artificial hair made by using polyamide as a raw material has good hair quality similar to that of human hair to some extent. In recent years, regarding hair quality of artificial hair, it has been required to reproduce the naturalness closer to that of human hair, and it has been required to further suppress the gloss of the fiber for artificial hair and bring the hair quality closer to that of human hair.

Therefore, an object of the present invention is to provide a technique relating to a fiber for artificial hair in which gloss is suppressed and the hair quality is closer to that of human hair.

Solution to Problem

According to the present invention, there is provided a fiber for artificial hair constituted of a resin composition containing an aliphatic polyamide and inorganic particles, in which in a particle size distribution of the inorganic particles measured by a laser diffraction method, a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more and 3.0 or less.

In addition, according to the present invention, there is provided a head accessory product using the above-mentioned fiber for artificial hair.

In addition, according to the present invention, there is provided a resin composition for artificial hair, including an aliphatic polyamide and inorganic particles, in which in a particle size distribution of the inorganic particles measured by a laser diffraction method, a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more and 3.0 or less.

Advantageous Effects of Invention

According to the present invention, it is possible to provide a technique relating to artificial hair in which gloss is suppressed and the hair quality is close to that of human hair.

DESCRIPTION OF EMBODIMENTS

Hereinafter, embodiments of the present invention will be described in detail.

The fiber for artificial hair according to an embodiment is constituted of a resin composition for artificial hair containing an aliphatic polyamide and inorganic particles. Hereinafter, components of the fiber for artificial hair and the resin composition for a fiber for artificial hair will be described in detail.

<Aliphatic Polyamide>

A resin composition constituting a fiber for artificial hair and a resin composition for artificial hair of the present embodiment contains an aliphatic polyamide.

The aliphatic polyamide is polyamide not containing an aromatic ring, and examples of the aliphatic polyamide include n-nylon formed by ring-opening polymerization of lactam, or n, m-nylon synthesized by a co-condensation polymerization reaction of an aliphatic diamine and an aliphatic dicarboxylic acid. The number of carbon atoms of lactam is preferably 6 to 12, and more preferably 6. The number of carbon atoms of the aliphatic diamine and the aliphatic dicarboxylic acid is preferably 6 to 12, and more preferably 6. The aliphatic diamine and the aliphatic dicarboxylic acid preferably have a functional group (amino group or carboxyl group) at both ends of the carbon atom chain, but the functional group may be provided at positions other than both ends. The carbon atom chain is preferably linear, but may have a branch. Examples of the aliphatic polyamide include polyamide 6 (nylon 6) and polyamide 66 (nylon 66). Polyamide 66 is preferable from a viewpoint of heat resistance.

Specifically, examples of the polyamide 6 include CM1007, CM1017, CM1017XL3, CM1017K, CM1026, and the like manufactured by Toray Industries, Inc. Examples of the polyamide 66 include CM3007, CM3001-N, CM3006, and CM3301L manufactured by Toray Industries, Inc., Zytel 101 and Zytel 42A manufactured by DuPont Co., Ltd., and Leona 1300S, 1500 and 1700 manufactured by Asahi Kasei Corporation.

A lower limit of a weight average molecular weight of the aliphatic polyamide is preferably 40,000 or more, more preferably 50,000 or more, and further more preferably 60,000 or more. An upper limit of the weight average molecular weight of the aliphatic polyamide is preferably 150,000 or less, more preferably 140,000 or less, and further more preferably 130,000 or less. By setting the weight average molecular weight of the aliphatic polyamide in the above range, the gloss of the obtained fiber for artificial hair can be suppressed, the tactile sensation can be made smooth, and the texture can be closer to that of human hair.

<Inorganic Particles>

The inorganic particles constituting the fiber for artificial hair and the resin composition for artificial hair of the present embodiment have a particle size distribution described below.

Specifically, in the inorganic particles constituting the fiber for artificial hair and the resin composition for artificial hair of the present embodiment, in a particle size distribution measured according to JIS R1629 by a laser diffraction method, a lower limit of a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more, preferably 1.9 or more, and more preferably 2.0 or more. In addition, an upper limit of the ratio ($D_{50}/D_{10}$) is 3.0 or less, preferably 2.7 or less, and more preferably 2.4 or less. By setting the ratio ($D_{50}/D_{10}$) to the above range, it is possible to suppress the gloss of the obtained fiber for artificial hair, and to obtain a texture closer to that of human hair.

The lower limit of $D_{50}$ of the inorganic particles is 3.0 μm or more, preferably 3.5 μm or more, and more preferably 4.0 μm or more. The upper limit of $D_{50}$ of the inorganic particles is 6.0 μm or less, more preferably 5.5 μm or less, and further more preferably 5.0 μm or less. By setting the value of $D_{50}$ of the inorganic particles to the above lower limit value or more, the appearance becomes good. On the other hand, by setting the value of $D_{50}$ of the inorganic particles to the above upper limit value or less, the tactile sensation can become good.

In addition, by setting $D_{50}$ of the inorganic particles in the above numerical value range, the balance between the gloss and the texture of the obtained fiber for artificial hair can become good.

The lower limit of $D_{10}$ of the inorganic particles is 1.5 μm or more, more preferably 1.7 μm or more, and further more preferably 1.9 μm or more. The upper limit of $D_{10}$ of the inorganic particles is 3.0 μm or less, more preferably 2.8 μm or less, and further more preferably 2.6 μm or less. By setting the value of $D_{10}$ of the inorganic particles to the above lower limit value or more, the appearance becomes good. On the other hand, by setting the value of $D_{10}$ of the inorganic particles to the above upper limit value or less, the tactile sensation can become good.

In addition, by setting $D_{10}$ of the inorganic particles in the above numerical value range, the balance between the gloss and the texture of the obtained fiber for artificial hair can become good.

Examples of a method of adjusting the ratio ($D_{50}/D_{10}$), and $D_{50}$ and $D_{10}$ within the above range include a method of classifying inorganic particles using a sieve having a predetermined opening.

Examples of the inorganic particles include fillers such as talc, mica, glass flakes, synthetic hydrotalcite, and kaolin. Among these, it is preferable to use talc as the inorganic particles from a viewpoint of suppressing the gloss of the obtained fiber for artificial hair. In addition, the talc is preferably contained in an amount of 90% by mass or more, more preferably 95% by mass or more, further more preferably 98% by mass or more, and particularly preferably 100% by mass with respect to the total inorganic particles.

A lower limit of a content of the inorganic particles with respect to 100 parts by mass of the aliphatic polyamide is preferably 0.5 parts by mass or more, more preferably 1.0 parts by mass or more, and further more preferably 1.5 parts by mass or more. On the other hand, an upper limit of the content of the inorganic particles with respect to 100 parts by mass of the aliphatic polyamide is preferably 10 parts by mass or less, more preferably 7 parts by mass or less, and further more preferably 5 parts by mass or less. By setting the content of the inorganic particles in the above range, it is possible to suppress the gloss of the fiber for artificial hair, and to make the tactile sensation or appearance closer to human hair.

The inorganic particles are preferably surface-treated with a silane coupling agent to be described later. In other words, it is preferable that the silane coupling agent is attached to surfaces of the inorganic particles. According to this, it is possible to further suppress the gloss.

The resin composition used in the present embodiment may contain additives, if necessary, for example, silane coupling agent, flame retardant, flame retardant aid, fine particles, heat resistant agent, light stabilizer, fluorescent agent, antioxidant, antistatic agent, pigment, dye, plasticizer, lubricant, and the like.

Examples of the above-mentioned silane coupling agent include epoxy silane, isocyanate silane, amino silane, mercapto silane, epoxy silane, vinyl silane, and methacryl silane. Among these, epoxy silane and amino silane are preferably used from a viewpoint of suppressing the gloss of the fiber for artificial hair.

Examples of the epoxy silane include 2-(3,4-epoxy cyclohexyl) ethyltrimethoxy silane, 3-glycidoxypropyltrimethoxy silane, and 3-glycidoxypropylmethyldiethoxy silane.

Examples of the amino silane include 3-aminopropyltrimethoxy silane, 3-aminopropyltriethoxy silane, N-2 (aminoethyl) 3-aminopropylmethyldimethoxy silane, N-2 (aminoethyl) 3-aminopropyltrimethoxy silane, N-phenyl-3-aminopropyltrimethoxy silane, and the like.

The glossiness of the fiber for artificial hair is preferably less than 70, more preferably 68 or less, and further more preferably 67 or less. With this, the balance between the appearance and the tactile sensation of the hair can become good.

(Method for Producing Fiber for Artificial Hair)

An example of a method for producing a fiber for artificial hair according to an embodiment will be described, but the present invention is not limited thereto.

First, the resin composition containing the above-mentioned aliphatic polyamide and the inorganic particles having the above-mentioned particle size distribution are melt-kneaded. As an apparatus for melt-kneading, various general kneading machines can be used. Examples of the melt-kneading include a single-screw extruder, a twin-screw extruder, a roll, a Banbury mixer, a kneader, and the like. Among these, the twin-screw extruder is preferable from a viewpoint of adjusting the degree of kneading and easiness of operation. The fiber for artificial hair of the present embodiment can be produced by melt-spinning by a normal melt-spinning method under appropriate temperature conditions depending on the type of polyamide.

In the case of melt spinning, not only a simple circular shape but also a spinning nozzle with a specially shaped nozzle hole can be used to cause the cross-sectional shape of the fiber for artificial hair to be heteromorphic such as cocoon-shaped, Y-shaped, H-shaped, X-shaped, petal-shaped, and the like.

The obtained undrawn yarn is subjected to a drawing treatment in order to improve a tensile strength of the fiber. The drawing treatment may include any method of a two-step method in which the undrawn yarn is once wound on a bobbin and then drawn in a step different from the melt spinning step, or a direct spinning drawing method in which the undrawn yarn is continuously drawn from the melt spinning step without being wound on the bobbin. In addition, the drawing treatment is performed by a one-step drawing method of performing drawing to a targeted drawing magnification at one time, or a multi-step drawing method of performing drawing to a targeted drawing magnification by performing drawing two or more times. As heating means in a case of performing heat drawing treatment, a heating roller, a heat plate, a steam jet device, a hot water tank, and the like can be used, and these can also be appropriately used in combination.

The lower limit of the fineness of the fiber for artificial hair of the present embodiment is preferably 10 dtex or more, more preferably 30 dtex or more, and further more preferably 35 dtex or more. In addition, the upper limit of the fineness of the fiber for artificial hair of the present embodiment is preferably 150 dtex or less, and more preferably 120 dtex or less. By setting the fineness of the fiber for artificial hair in the above range, it is possible to make the tactile sensation smoother while suppressing the gloss.

With the fiber for artificial hair described above, it is possible to bring the hair quality closer to that of human hair while suppressing the gloss.

(Head Accessory Product)

The above-mentioned fiber for artificial hair is suitably used as a fiber constituting a head accessory product. The head accessory product is an ornament that decorates a person's head, and is specifically a wig, a partial wig, a hair piece, a blade, an extension hair, a doll hair, a ribbon, a bead, and the like.

Hereinabove, the embodiments of the present invention have been described above, but these are examples of the present invention and various configurations other than the above can be adopted.

EXAMPLE 1

Hereinafter, the present invention will be described with reference to examples and comparative examples, but the present invention is not limited thereto.

<Polyamide>

As polyamide, nylon 66: MILAN CM3001-N (weight average molecular weight Mw: 50,000), manufactured by Toray Industries, Inc. was used. The weight average molecular weight Mw was measured with the following equipment and conditions.

Used apparatus: Pump . . . shodex DS-4, column . . . shodex GPC HFIP-806M×2+HFIP-803

Detector . . . shodex RI-71

Eluent: Hexafluoroisopropanol (+additive $CF_3COONa$ (5 mmol/L))

Pre-treatment: Filtration with membrane filter (0.2 μm)

Concentration: 0.2 w/v %

Injection amount: 100 μL

Column temperature: 40° C.

Flow rate: 1.0 mL/min

Standard substance: Standard polymethylmethacrylate (PMMA)

A calibration curve was prepared by standard PMMA, and a weight average molecular weight Mw was expressed by PMMA conversion value.

<Inorganic Particles>

A plurality of types of inorganic particles shown in Tables 1-1 and 1-2 were prepared. For talc, a plurality of types of talc having different particle sizes was used as follows.

Examples 1, 5, 6, 8, 9: P-4, manufactured by Nippon Talc Co., Ltd.

In Example 5, 100 parts by mass of talc and 3 parts by mass of epoxy silane ("KBM-403" manufactured by Shin-Etsu Silicone) were heat-stirred to prepare talc treated with epoxy silane of 3% throughput (3% epoxy silane-treated talc). In Example 6, talc treated with amino silane was prepared in the same manner as in Example 5, except that amino silane (KBE-903, 3-aminopropyltriethoxy silane, manufactured by Shin-Etsu Chemical Co., Ltd.) was used instead of epoxy silane (3% amino silane-treated talc).

Example 2: P-3, manufactured by Nippon Talc Co., Ltd.

Example 3: PAOG-3, manufactured by Nippon Talc Co., Ltd.

Example 4: P-6, manufactured by Nippon Talc Co., Ltd.

Examples 7, 10 and 11: Synthetic talc was prepared according to a known method disclosed in Japanese Unexamined Patent Publication No. 2011-73901, and a predetermined particle size distribution shown in Tables 1-1 and 1-2 was obtained using a classifier.

Example 12: Synthetic mica was prepared according to the method disclosed in Japanese Unexamined Patent Publication No. H11-240714, and a predetermined particle size distribution shown in Tables 1-1 and 1-2 was obtained using a classifier.

Example 13: Glass flakes were prepared according to the method disclosed in Japanese Unexamined Patent Publication No. 2015-214478, and a predetermined particle size distribution shown in Tables 1-1 and 1-2 was obtained using a classifier.

Example 14: Synthetic kaolin was prepared according to the method disclosed in Japanese Unexamined Patent Publication No. 2001-172529, and a predetermined particle size distribution shown in Tables 1-1 and 1-2 was obtained using a classifier.

Comparative Example 1: SG-200, manufactured by Nippon Talc Co., Ltd.

Comparative Example 2: SG-2000, manufactured by Nippon Talc Co., Ltd.

Comparative Example 3: Synthetic talc was prepared according to a known method disclosed in Japanese Unexamined Patent Publication No. 2011-73901, and a predetermined particle size distribution shown in Tables 1-1 and 1-2 was obtained using a classifier.

<Particle Size Distribution of Inorganic Particles>

A particle size distribution of each inorganic particle was measured by a laser diffraction method (LA-920, manufactured by HORIBA, Ltd.) according to JIS R1629. Tables 1-1 and 1-2 show $D_{50}$, which is a particle size equivalent to a cumulative percentage of 50% based on the volume of each inorganic particle, $D_{10}$, which is a particle size equivalent to a cumulative percentage of 10% based on the volume, and a ratio ($D_{50}/D_{10}$).

(Preparation of Fiber for Artificial Hair)

Each component was mixed with a tumbler mixer so as to have components and blending amounts shown in Tables 1-1 and 1-2, and kneaded using a φ30 mm twin-screw extruder to obtain raw material pellets for spinning.

Then, after dehumidifying and drying the pellets so that the water absorption rate was 1,000 ppm or less, spinning was performed using a φ40 mm single-shaft melt-spinning device, and while cooling a molten resin discharged from a die having a hole diameter of 0.5 mm/piece through a water tank at about 30° C., a discharge amount and a winding speed were adjusted to prepare an undrawn yarn having a set fineness. A set temperature of the φ40 mm melt-spinning device was appropriately adjusted according to a proportion of an addition amount of aliphatic polyamides and semi-aromatic polyamides.

The obtained undrawn yarn was drawn at 100° C., and then annealed at 180° C. to obtain a fiber for artificial hair having a predetermined fineness. Drawing was performed at a drawing magnification of 3 times and a relaxation rate at a time of annealing of 5%. The relaxation rate at the time of annealing is a value calculated by (rotational speed of the take-up roller at the time of annealing)/(rotational speed of the feeding roller at the time of annealing).

The obtained fiber for artificial hair was evaluated as described later. The evaluation results are shown in Tables 1-1 and 1-2.

(Glossiness)

The glossiness of the fiber for artificial hair of each example and each comparative example was measured with the following devices and conditions. The obtained results are shown in Tables 1-1 and 1-2.

Device: Variable angle photometer GP-700 manufactured by Murakami Color Research Laboratory Incident angle: 45°

Sensitivity adjustment dial value (COARSE): 718

Sensitivity adjustment dial value (FINE): 737

(Hair Quality (Appearance))

Whether or not the appearance of the fiber for artificial hair is closer to that of human hair was determined by a treatment technician of a fiber for artificial hair. Those evaluated to have an appearance very close to that of human hair were rated as "A", those evaluated to have an appearance slightly different from but close to that of human hair were rated as "B", and those evaluated to have an appearance clearly different from that of human hair were rated as "C". The evaluation results of appearance are shown in Tables 1-1 and 1-2.

(Hair Quality (Tactile Sensation))

The "tactile sensation" is the sensation when the fiber for artificial hair is touched, and was determined by a treatment technician of a fiber for artificial hair. Those evaluated that the touch was very smooth and the tactile sensation was particularly good were rated as "A", those evaluated that the smoothness was slightly poor but the tactile sensation was good were rated as "B", and those evaluated that the touch was not smooth and the tactile sensation was not good were rated as "C". The evaluation results of tactile sensation are shown in Tables 1-1 and 1-2.

TABLE 1-1

|  |  | Example 1 | Example 2 | Example 3 | Example 4 | Example 5 | Example 6 | Example 7 | Example 8 | Example 9 |
|---|---|---|---|---|---|---|---|---|---|---|
|  | Polyamide: nylon 66 (parts by mass) | 100 | 100 | 100 | 100 | 100 | 100 | 100 | 100 | 100 |
| Inorganic particles | Talc (parts by mass) | 3 | 3 | 3 | 3 | 3 | 3 | 3 | 0.8 | 8 |
|  | Synthetic mica (parts by mass) | — | — | — | — | — | — | — | — | — |
|  | Glass flakes (parts by mass) | — | — | — | — | — | — | — | — | — |
|  | Synthetic kaolin (parts by mass) | — | — | — | — | — | — | — | — | — |
| Inorganic particles particle size division | $D_{10}$ (μm) | 1.9 | 2.2 | 1.9 | 1.9 | 1.9 | 1.9 | 2.3 | 1.9 | 1.9 |
|  | $D_{50}$ (μm) | 4.5 | 5.0 | 4.8 | 4.2 | 4.5 | 4.5 | 4.3 | 4.5 | 4.5 |
|  | $D_{50}/D_{10}$ | 2.4 | 2.3 | 2.5 | 2.2 | 2.4 | 2.4 | 1.9 | 2.4 | 2.4 |
|  | Surface treatment of inorganic particles | None | None | None | None | Epoxy silane | Amino silane | None | None | None |
| Evaluation | Glossiness | 52 | 50 | 52 | 50 | 30 | 30 | 49 | 63 | 32 |
|  | Hair quality (appearance) | A | A | A | A | A | A | A | A | A |
|  | Hair quality (tactile sensation) | A | A | A | A | A | A | A | A | A |

TABLE 1-2

|  |  | Example 10 | Example 11 | Example 12 | Example 13 | Example 14 | Comparative Example 1 | Comparative Example 2 | Comparative Example 3 |
|---|---|---|---|---|---|---|---|---|---|
|  | Polyamide: nylon 66 (parts by mass) | 100 | 100 | 100 | 100 | 100 | 100 | 100 | 100 |
| Inorganic particles | Talc (parts by mass) | 3 | 3 | — | — | — | 3 | 3 | 3 |
|  | Synthetic mica (parts by mass) | — | — | 3 | — | — | — | — | — |
|  | Glass flakes (parts by mass) | — | — | — | 3 | — | — | — | — |
|  | Synthetic kaolin (parts by mass) | — | — | — | — | 3 | — | — | — |

TABLE 1-2-continued

|  |  | Example 10 | Example 11 | Example 12 | Example 13 | Example 14 | Comparative Example 1 | Comparative Example 2 | Comparative Example 3 |
|---|---|---|---|---|---|---|---|---|---|
| Inorganic particles particle size division | $D_{10}$ (μm) | 0.7 | 3.8 | 2.0 | 2.1 | 2 | 0.8 | 0.1 | 2.8 |
|  | $D_{50}$ (μm) | 2.0 | 8.0 | 4.5 | 4.2 | 4.1 | 2.7 | 0.9 | 4.4 |
|  | $D_{50}/D_{10}$ | 2.9 | 2.1 | 2.3 | 2.0 | 2.1 | 3.4 | 9.0 | 1.6 |
| Surface treatment of inorganic particles |  | None | None | None | None | None | None | None | None |
| Evaluation | Glossiness | 58 | 51 | 64 | 64 | 65 | 70 | 72 | 75 |
|  | Hair quality (appearance) | B | A | A | A | A | C | C | C |
|  | Hair quality (tactile sensation) | A | B | A | A | A | B | C | B |

As shown in Tables 1-1 and 1-2, it was confirmed that the fibers for artificial hair of Examples 1 to 14 had a significantly lower glossiness than the fibers for artificial hair of Comparative Examples 1 to 3. In addition, it was confirmed that the fibers for artificial hair of Examples 1 to 14 had good hair quality in both appearance and tactile sensation, and among these, the fibers for artificial hair of Examples 1 to 9 and Examples 12 to 14 had appearance very closer to that of human hair and had particularly good tactile sensation. On the other hand, it was confirmed that in Comparative Examples 1 and 3, the appearance was different from that of human hair, and in Comparative Example 2, the appearance was different from that of human hair and the tactile sensation was poor.

Priority is claimed on Japanese Patent Application No. 2019-024819, filed on Feb. 14, 2019, the content of which is incorporated herein by reference.

The invention claimed is:

1. A fiber for artificial hair comprising:
   a resin composition containing an aliphatic polyamide and inorganic particles,
   wherein in a particle size distribution of the inorganic particles measured by a laser diffraction method, a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more and 3.0 or less, and
   $D_{10}$ of the inorganic particles is 1.5 μm or more and 3.0 μm or less.

2. The fiber for artificial hair according to claim 1, wherein $D_{50}$ of the inorganic particles is 3.0 μm or more and 6.0 μm or less.

3. The fiber for artificial hair according to claim 1, wherein the resin composition further contains a silane coupling agent.

4. The fiber for artificial hair according to claim 3, wherein the silane coupling agent is epoxy silane or amino silane.

5. The fiber for artificial hair according to claim 1, wherein the inorganic particles are talc.

6. The fiber for artificial hair according to claim 1, wherein the aliphatic polyamide is one or both of nylon 6 and nylon 66.

7. A head accessory product using the fiber for artificial hair according to claim 1.

8. A resin composition for artificial hair comprising:
   an aliphatic polyamide; and
   inorganic particles,
   wherein in a particle size distribution of the inorganic particles measured by a laser diffraction method, a ratio ($D_{50}/D_{10}$) of $D_{50}$, which is a particle size equivalent to a cumulative percentage of 50% based on volume, to $D_{10}$, which is a particle size equivalent to a cumulative percentage of 10% based on volume, is 1.8 or more and 3.0 or less, and
   $D_{10}$ of the inorganic particles is 1.5 μm or more and 3.0 μm or less.

9. The fiber for artificial hair according to claim 1, wherein $D_{50}/D_{10}$ is 1.9 or more and 2.7 or less.

10. The fiber for artificial hair according to claim 1, wherein $D_{50}/D_{10}$ is 2.0 or more and 2.4 or less.

11. The fiber for artificial hair according to claim 1, wherein $D_{50}$ is 3.0 μm or more and 6.0 or less.

12. The fiber for artificial hair according to claim 1, wherein $D_{50}$ is 3.5 μm or more and 5.5 μm or less.

13. The fiber for artificial hair according to claim 1, wherein $D_{50}$ is 4.0 μm or more and 5.0 μm or less.

14. The fiber for artificial hair according to claim 1, wherein $D_{10}$ is 1.5 μm or more and 3.0 μm or less.

15. The fiber for artificial hair according to claim 1, wherein $D_{10}$ is 1.7 μm or more and 2.8 μm or less.

16. The fiber for artificial hair according to claim 1, wherein $D_{10}$ is 1.9 μm or more and 2.6 μm or less.

17. The fiber for artificial hair according to claim 1, wherein the content of inorganic particles in 100 mass parts of the aliphatic polyamide is 0.5 mass parts or more and 10 mass parts or less.

\* \* \* \* \*